United States Patent [19]

Short

[11] Patent Number: 6,004,788
[45] Date of Patent: *Dec. 21, 1999

[54] ENZYME KITS AND LIBRARIES

[75] Inventor: Jay M. Short, Encinitas, Calif.

[73] Assignee: Diversa Corporation, San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/503,606

[22] Filed: Jul. 18, 1995

[51] Int. Cl.$^6$ ...................................................... C12N 9/00
[52] U.S. Cl. .............................. 435/183; 435/4; 435/189; 435/190; 435/191; 435/193; 435/194; 435/195; 435/212; 435/232
[58] Field of Search ................................ 435/4, 183, 189, 435/190, 191, 193, 195, 232, 194, 212

[56] References Cited

U.S. PATENT DOCUMENTS

| | | | |
|---|---|---|---|
| 3,878,302 | 4/1975 | Luksas et al. | 426/46 |
| 5,605,793 | 2/1997 | Stemmer | 435/6 |
| 5,811,238 | 9/1998 | Stemmer et al. | 435/6 |
| 5,830,721 | 11/1998 | Stemmer et al. | 435/172.1 |
| 5,837,458 | 11/1998 | Minshull et al. | 435/6 |

FOREIGN PATENT DOCUMENTS

WO 91/16427  10/1997  WIPO.

OTHER PUBLICATIONS

GibcoBRL Life Technologies 1993–1994 Molecular Biology Catalogue. pp. 11–3 to 11–4, 1993.
Boehringer Mannheim Corporation, 1992 Biochemical Catalog.
Barnes, S.M. et al. "Remarkable archaeal diversity detected in a Yellowstone National Park hot spring environment." Proceedings of the National Academy of Sciences, USA (Mar. 1994), vol. 91, pp. 1609–1613.

*Primary Examiner*—Ponnathapura Achutamurthy
*Assistant Examiner*—Nashaat T. Nashed
*Attorney, Agent, or Firm*—Gray Cary Ware & Freidenrich; Lisa A. Haile

[57] ABSTRACT

Recombinant enzyme libraries and kits where a plurality of enzymes are each characterized by different physical and/or chemical characteristics and classified by common characteristics. The characteristics are determined by screening of recombinant enzymes expressed by a DNA library produced from various microorganisms.

2 Claims, 4 Drawing Sheets

ENZYME KITS AND LIBRARIES

This invention relates to enzyme libraries and kits and to the preparation thereof. More particularly, the present invention is directed to recombinant enzyme expressions libraries, recombinant enzyme libraries and kits prepared therefrom which recombinant enzymes are generated from DNA obtained from microorganisms.

Industry has recognized the need for new enzymes for a wide variety of industrial applications. As a result, a variety of microorganisms have been screened to ascertain whether or not such microorganisms have a desired enzyme activity. If such microorganism does have a desired enzyme activity, the enzyme is then recovered from the microorganism.

In accordance with the present invention, there is provided a novel approach for obtaining enzymes for further use, for example, for packaging into kits for further research. In accordance with the present invention, recombinant enzymes are generated from microorganisms and are classified by various enzyme characteristics. In this manner, the enzymes can be provided as packaged enzyme screening kits, with enzymes in the kit being grouped to have selected enzyme characteristics.

More particularly, in accordance with an aspect of the present invention there is provided a recombinant expression library which is comprised of a multiplicity of clones which are capable of expressing recombinant enzymes. The expression library is produced by recovering DNA from a microorganism, cloning such DNA into an appropriate expression vector which is then used to transfect or transform an appropriate host for expression of a recombinant protein.

Thus, for example, genomic DNA may be recovered from either a culturable or non-culturable organism and employed to produce an appropriate recombinant expression library for subsequent determination of enzyme activity.

In accordance with an aspect of the present invention, such recombinant expression library may be prepared without prescreening the organism from which the library is prepared for enzyme activity.

Having prepared a multiplicity of recombinant expression clones from DNA isolated from an organism, the polypeptides expressed by such clones are screened for enzyme activity and specified enzyme characteristics in order to identify and classify the recombinant clones which produce polypeptides having specified enzyme characteristics.

In accordance with a preferred aspect of the present invention, the recombinant enzymes are characterized by both physical and chemical characteristics and such chemical characteristics are preferably classified in a tiered manner such that recombinant enzymes having a chemical characteristic in common are then classified by other chemical characteristics which may or may not be more selective or specific chemical characteristic and so on, as hereinafter indicated in more detail.

As hereinabove indicated, the recombinant enzymes are also preferably classified by physical characteristics and one or more tiers of the enzymes which are classified by chemical characteristics may also be classified by physical characteristics or vice versa.

As used herein, the term "chemical characteristic" of a recombinant enzyme refers to the substrate or chemical functionality upon which the enzyme acts and/or the catalytic reaction performed by the enzyme; e.g., the catalytic reaction may be hydrolysis (hydrolases) and the chemicals functionality may be the type of bond upon which the enzyme acts (esterases cleave ester bonds) or may be the particular type of structure upon which the enzyme acts (a glycosidase which acts on glycosidic bonds). Thus, for example, a recombinant enzyme which acts on glycosidic bonds may, for example, be chemically classified in accordance with the tiered system as: Tier 1: hydrolase; Tier 2: acetal bonds; Tier 3: glycosidase.

As used herein, a "physical characteristic" with respect to a recombinant enzyme means a property (other than a chemical reaction) such as pH; temperature stability; optimum temperature for catalytic reaction; organic solvent tolerance; metal ion selectivity; detergent sensitivity, etc.

In an embodiment of the invention, in which a tiered approach is employed for classifying the recombinant enzymes by chemical and/or physical characteristics, the enzymes at one or more of the chemical characteristic tiers may also be classified by one or more physical characteristics and vice versa. In a preferred embodiment, the enzymes are classified by both physical and chemical characteristics, e.g., the individual substrates upon which they act as well as physical characteristics.

Thus, for example, as a representative example of the manner in which a recombinant enzyme may be classified in accordance with the present invention, a recombinant enzyme which is a protease (in this illustration Tier 1 is hydrolase; Tier 2 is amide (peptide bond) that may be further classified in Tier 3 as to the ultimate site in the amino acid sequence where cleavage occurs; e.g., anion, cation, large hydrophobic, small hydrophobic. Each of the recombinant enzymes which has been classified by the side chain in Tier 3 may also be further classified by physical characteristics of the type hereinabove indicated.

In this manner, it is possible to select from the recombinant library, enzymes which have a specified chemical characteristic in common, e.g., all endopeptidases (which act on internal peptide bonds) and which have a specified physical characteristic in common, e.g., all act optimally at a pH within a specified range.

As hereinabove indicated, a recombinant enzyme library prepared from a microorganism is preferably classified by chemical characteristics in a tiered approach. This may be accomplished by initially testing the recombinant polypeptides generated by the library in a low selectivity screen, e.g., the catalytic reaction performed by the enzyme. This may be conveniently accomplished by screening for one or more of the six IUB classes; Oxidoreductases; transferases; hydrolases; lyases, isomerases, ligases.

The recombinant enzymes which are determined to be positive for one or more of the IUB classes may then be rescreened for a more specific enzyme activity.

Thus, for example, if the recombinant library is screened for hydrolase activity, then those recombinant clones which are positive for hydrolase activity may be rescreened for a more specialized hydrolase activity, i.e., the type of bond on which the hydrolase acts. Thus, for example, the recombinant enzymes which are hydrolases may be rescreened to ascertain those hydrolases which act on one or more specified chemical functionalities, such as: (a) amide (peptide bonds), i.e., proteases; (b) ester bonds, i.e., esterases and lipases; (c) acetals, i.e., glycosidases, etc.

The recombinant enzymes which have been classified by the chemical bond on which they act may then be rescreened to determine a more specialized activity therefor, such as the type of substrate on which they act.

Thus, for example, those recombinant enzymes which have been classified as acting on ester bonds (lipases and esterases) may be rescreened to determine the ability thereof to generate optically active compounds, i.e., the ability to act on specified substrates, such as meso alcohols, meso diacids, chiral alcohols, chiral acids, etc.

For example, the recombinant enzymes which have been classified as acting on acetals may be rescreened to classify such recombinant enzymes by a specific type of substrate upon which they act, e.g., (a) P1 sugar such as glucose, galactose, etc., (b) glucose polymer (exo-, endo- or both), etc.

Enzyme Tiers

Thus, as a representative but not limiting example, the following are representative enzyme tiers:

TIER 1. Divisions are based upon the catalytic reaction performed by the enzyme, e.g., hydrolysis, reduction, oxidation, etc. The six IUB classes will be used: Oxidoreductase, Transferases, Hydrolases, Lyases, Isomerases, Ligases.

TIER 2: Divisions are based upon the chemical functionality undergoing reaction, e.g., esters, amides, phosphate diesters, sulfate mono esters, aldehydes, ketones, alcohols, acetals, ketals, alkanes, olefins, aromatic rings, heteroaromatic rings, molecular oxygen, enols, etc.

Lipases and esterases both cleave the ester bond; the distinction comes in whether the natural substrate is aggregated into a membrane (lipases) or dispersed into solution (esterases).

TIER 3: Divisions and subdivisions are based upon the differences between individual substrate structures which are covalently attached to the functionality undergoing reaction as defined in Tier 2. For example acetal hydrolysis: is the acetal part of glucose or galactose; or is the acetal the $\alpha$ or $\beta$ anomer? These are the types of distinctions made in TIER 3. The divisions based upon substrate specificity are unique to each particular enzyme reaction; there will be different substrate distinctions depending upon whether the enzyme is, for example, a protease or phosphatase.

TIER 4: Divisions are based on which of the two possible enantiomeric products the enzyme produces. This is a measure of the ability of the enzyme to selectively react with one of the two enantiomers (kinetic resolution), or the ability of the enzyme to react with a meso difunctional compound to selectively generate one of the two enantiomeric reaction products.

TIER 5/ORTHOGONAL TIER/PHYSICAL CHARACTER TIER.

The fifth tier is orthogonal to the other tiers. It is based on the physical properties of the enzymes, rather than the chemical reactions, per se: The fifth Tier forms a second dimension with which to classify the enzymes. The Fifth Tier can be applied to any of the other Tiers, but will most often be applied to the Third Tier.

Thus, in accordance with an aspect of the present invention, an expression library is randomly produced from the DNA of a microorganism, in particular, the genomic DNA, or cDNA of the microorganism and the recombinant proteins or polypeptides produced by such expression library are screened to classify the recombinant enzymes by different enzyme characteristics. In a preferred embodiment, the recombinant proteins are screened for one or more particular chemical characteristics and the enzymes identified as having such characteristics are then rescreened for a more specific chemical characteristic and this rescreening may be repeated one or more times. In addition, in a preferred embodiment, the recombinant enzymes are also screened to classify such enzymes by one or more physical characteristics. In this manner, the recombinant enzymes generated from the DNA of a microorganism are classified by both chemical and physical characteristics and it is therefore possible to select recombinant enzymes from one or more different organisms that have one or more common chemical characteristics and/or one or more common physical characteristics. Moreover, since such enzymes are recombinant enzymes, it is possible to produce such enzymes in desired quantities and with a desired purity.

The tiered approach of the present invention is not limited to a tiered approach in which, for example, the tiers are more restrictive. For example, the tiered approach is also applicable to using a tiered approach in which, for example, the first tier is "wood degrading" enzymes. The second chemical tier could then, for example, be the type of enzyme which is a "wood degrading" enzyme.

Similarly, the first tier or any other tier could be physical characteristics and the next tier could be specified chemical characteristics.

Thus, the present invention is generally applicable to providing recombinant enzymes and recombinant enzyme libraries wherein various enzymes are classified by different chemical and/or physical characteristics.

The microorganisms from which the recombinant libraries may be prepared include prokaryotic microorganisms, such as Eubacteria and Archaebacteria, and lower eukaryotic microorganisms such as fungi, some algae and protozoa. The microorganisms may be cultured microorganisms or uncultured microorganisms obtained from environmental samples and such microorganisms may be extremophiles, such as thermophiles, hyperthermophiles, psychrophiles, psychrotrophs, etc.

The recombinant enzymes in the library which are classified as hereinabove described may or may not be sequenced and may or may not be in a purified form. Thus, in accordance with the present invention, it is possible to classify one or more of the recombinant enzymes before or after obtaining the sequence of the enzyme or before or after purifying the enzyme to essential homogeneity.

The screening for chemical characteristics may be effected on individual expression clones or may be initially effected on a mixture of expression clones to ascertain whether or not the mixture has one or more specified enzyme activities. If the mixture has a specified enzyme activity, then the individual clones may be rescreened for such enzyme activity or for a more specific activity. Thus, for example, if a clone mixture has hydrolase activity, then the individual clones may be recovered and screened to determine which of such clones has hydrolase activity.

The present invention is also directed to preparing and providing enzyme kits for use in further screening and/or research. Thus, in accordance with an aspect of the invention, a reagent package or kit is prepared by placing in the kit or package, e.g., in suitable containers, at least three different recombinant enzymes with each of the at least three different recombinant enzymes having at least two enzyme characteristics in common. In a preferred embodiment, one common characteristic is a chemical characteristic or property and the other common characteristic is a physical characteristic or property; however, it is possible to prepare kits which have two or more chemical characteristics or properties in common and no physical characteristics or property in common and vice versa.

Since, in accordance with the present invention, it is possible to provide a recombinant enzyme library from one or more microorganisms which is classified by a multiplicity of chemical and/or physical properties, a variety of enzyme kits or packages can be prepared having a variety of selected chemical and/or physical characteristics which can be formulated to contain three or more recombinant enzymes in which at least three and preferably all of the recombinant enzymes have in common at least one chemical characteristic and have in common at least one physical characteristic. The kit should contain an appropriate label specifying such common characteristics.

In one embodiment, at least three recombinant enzymes in the kit have in common the most specific chemical characteristic specified on the label. The term "label" is used in its broadest sense and includes package inserts or literature associated or distributed in conjunction with the kit or package. Thus, for example, if the kit is labeled for a specific substrate (one of the Tier 3 examples above), then for example, at least three of the enzymes in the kit would act on such substrate.

The kits will preferably contain more than three enzymes, for example, five, six or more enzymes and in a preferred embodiment at least three and preferably a majority and in some cases all of the recombinant enzymes in the kit will have at least two enzyme properties or characteristics in common, as hereinabove described.

The recombinant enzymes in the kits may have two or more enzymes in a single container or individual enzymes in individual containers or various combinations thereof.

As hereinabove indicated, the expression library may be produced from environmental samples in which case DNA may be recovered without culturing of an organism or the DNA may be recovered from a cultured organism.

In preparing the expression library genomic DNA may be recovered from either a cultured organism or an environmental sample (for example, soil) by various procedures. The recovered or isolated DNA is then fragmented into a size suitable for producing an expression library and for providing a reasonable probability that desired genes will be expressed and screened without the necessity of screening an excessive number of clones. Thus, for example, if the average genome fragment produced by shearing is 4.5 kbp, for a 1.8 Mbp genome about 2000 clones should be screened to achieve about a 906 probability of obtaining a particular gene. In some cases, in particular where the DNA is recovered without culturing, the DNA is amplified (for example by PCR) after shearing.

The sized DNA is cloned into an appropriate expression vector and transformed into an appropriate host, preferably a bacterial host and in particular E. coli. Although E. coli is preferred, a wide variety of other hosts may be used for producing an expression library.

The expression vector which is used is preferably one which includes a promoter which is known to function in the selected host in case the native genomic promoter does not function in the host.

As representative examples of expression vectors which may be used for preparing an expression library, there may be mentioned phage, plasmids, phagemids cosmids, phosmids, bacterial artificial chromosomes, P1-based artificial chromosomes, yeast artificial chromosomes, and any other vectors specific for specific hosts of interest (such as bacillus, aspergillus, yeast, etc.) The vector may also include a tag of a type known in the art to facilitate purification.

The following outlines a general procedure for producing expression libraries from both culturable and non-culturable organisms.

CULTURABLE ORGANISMS
Obtain Biomass
DNA Isolation cetyltrimethylammonium bromide (CTAB)
Shear DNA (25 gauge needle)
Blunt DNA (Mung Bean Nuclease)
Methylate (EcoR I Methylase)
Ligate to EcoR I linkers (GGAATTCC)
Cut back linkers (EcoR I Restriction Endonuclease)
Size Fractionate (Sucrose Gradient)
Ligate to lambda vector (Lambda ZAP® (Stratagene) and gt11)
Package (in vitro lambda packaging extract)
Plate on E. coli host and amplify UNCULTURABLE ORGANISMS
Obtain cells
Isolate DNA (Various Methods)
Blunt DNA (Mung Bean Nuclease)
Ligate to adaptor containing a Not I site and conjugated to magnetic beads
Ligate unconjugated adaptor to the other end of the DNA
Amplify DNA in a reaction which allows for high fidelity, and
uses adaptor sequences as primers
Cut DNA with Not I
Size fractionate (Sucrose Gradient or Sephacryl® (polyacrylamide) Column)
Ligate to lambda vector (Lambda (Stratagene) and gt11)
Package (in vitro lambda packaging extract)
Plate on E. coli host and amplify The expression libraries may be screened for one or more selected chemical characteristics. Selected representative chemical characteristics are described below but such characteristics do not limit the present invention. Moreover, the expression libraries may be screened for some or all of the characteristics. Thus, some of the chemical characteristics specified herein may be determined in all of the libraries, none of the libraries or in only some of the libraries.

The recombinant enzymes may also be tested and classified by physical properties. For example, the recombinant enzymes may be classified by physical properties such as follows:

pH Optima
<3
3–6
6–9
9–12
>12

Temperature Optima
>90° C.
75–90° C.
60–75° C.
45–60° C.
30–45° C.
15–30° C.
0–15° C.

Temperature Stability
half-life at:
90° C.
75° C.
60° C.
45° C.

Organic Solvent Tolerance
water miscible
(DMF)
90%
75%
45%
30% water immiscible
hexane
toluene

Metal Ion Selectivity
EDTA—10 mM
$Ca^{+2}$—1 mM
$Mg^{+2}$—100 µM
$Mn^{+2}$—10 µM
$Co^{+3}$—10 µM Detergent Sensitivity
neutral (triton)
anionic (deoxycholate)
cationic (CHAPS)

The recombinant enzymes of the libraries and kits of the present invention may be used for a variety of purposes and the present invention by providing a plurality of recombinant enzymes classified by a plurality of different enzyme characteristics permits rapid screening of enzymes for a variety of applications. Thus, for example, the present invention permits assembly of enzyme kits which contain a plurality of enzymes which are capable of operating on a specific bond or a specific substrate at specified conditions to thereby enable screening of enzymes for a variety of applications. As representative examples of such applications, there may be mentioned:

1 Lipase/Esterase
   a. Enantioselective hydrolysis of esters (lipids)/thioesters
      1) Resolution of racemic mixtures
      2) Synthesis of optically active acids or alcohols from meso-diesters
   b. Selective syntheses
      1) Regiospecific hydrolysis of carbohydrate esters
      2) Selective hydrolysis of cyclic secondary alcohols
   c. Synthesis of optically active esters, lactones, acids, alcohols
      1) Transesterification of activated/nonactivated esters
      2) Interesterification
      3) Optically active lactones from hydroxyesters
      4) Regio- and enantioselective ring opening of anhydrides
   d. Detergents
   e. Fat/Oil conversion
   f. Cheese ripening 2 Protease
   a. Ester/amide synthesis
   b. Peptide synthesis
   c. Resolution of racemic mixtures of amino acid esters
   d. Synthesis of non-natural amino acids
   e. Detergents/protein hydrolysis 3 Glycosidase/Glycosyl Transferase
   a. Sugar/polymer synthesis
   b. Cleavage of glycosidic linkages to form mono, di- and oligosaccharides
   c. Synthesis of complex oligosaccharides
   d. Glycoside synthesis using UDP-galactosyl transferase
   e. Transglycosylation of disaccharides, glycosyl fluorides, aryl galactosides
   f. Glycosyl transfer in oligosaccharide synthesis
   g. Diastereoselective cleavage of β-glucosylsulfoxides
   h. Asymmetric glycosylations
   i. Food processing
   j. Paper processing 4 Phosphatase/Kinase
   a. Synthesis/hydrolysis of phosphate esters
      1) Regio-, enantioselective phosphorylation
      2) Introduction of phosphate esters
      3) Synthesize phospholipid precursors
      4) Controlled polynucleotide synthesis
   b. Activate biological molecule
   c. Selective phosphate bond formation without protecting groups 5 Mono/Dioxygenase
   a. Direct oxyfunctionalization of unactivated organic substrates
   b. Hydroxylation of alkane, aromatics, steroids
   c. Epoxidation of alkenes
   d. Enantioselective sulphoxidation
   e. Regio- and stereoselective Bayer-Villiger oxidations 6 Haloperoxidase
   a. Oxidative addition of halide ion to nucleophilic sites
   b. Addition of hypohalous acids to olefinic bonds
   c. Ring cleavage of cyclopropanes
   d. Activated aromatic substrates converted to ortho and para derivatives
   e. 1.3 diketones converted to 2-halo-derivatives
   f. Heteroatom oxidation of sulfur and nitrogen containing substrates
   g. Oxidation of enol acetates, alkynes and activated aromatic rings 7 Lignin peroxidase/Diarylpropane peroxidase
   a. Oxidative cleavage of C—C bonds
   b. Oxidation of benzylic alcohols to aldehydes
   c. Hydroxylation of benzylic carbons
   d. Phenol dimerization
   e. Hydroxylation of double bonds to form diols
   f. Cleavage of lignin aldehydes 8 Epoxide Hydrolase
   a. Synthesis of enantiomerically pure bioactive compounds
   b. Regio- and enantioselective hydrolysis of epoxide
   c. Aromatic and olefinic epoxidation by monooxygenases to form epoxides
   d. Resolution of racemic epoxides
   e. Hydrolysis of steroid epoxides 9 Nitrile Hydratase/Nitrilase
   a. Hydrolysis of aliphatic nitriles to carboxamides
   b. Hydrolysis of aromatic, heterocyclic, unsaturated aliphatic nitriles to corresponding acids
   c. Hydrolysis of acrylonitrile
   d. Production of aromatic and carboxamides, carboxylic acids (nicotinamide, picolinamide, isonicotinamide)
   e. Regioselective hydrolysis of acrylic dinitrile
   f. α-amino acids from α-hydroxynitriles 10 Transaminase
   a. Transfer of amino groups into oxo-acids 11 Amidase/Acylase
   a. Hydrolysis of amides, amidines, and other C—N bonds
   b. Non-natural amino acid resolution and synthesis

Figure 1:
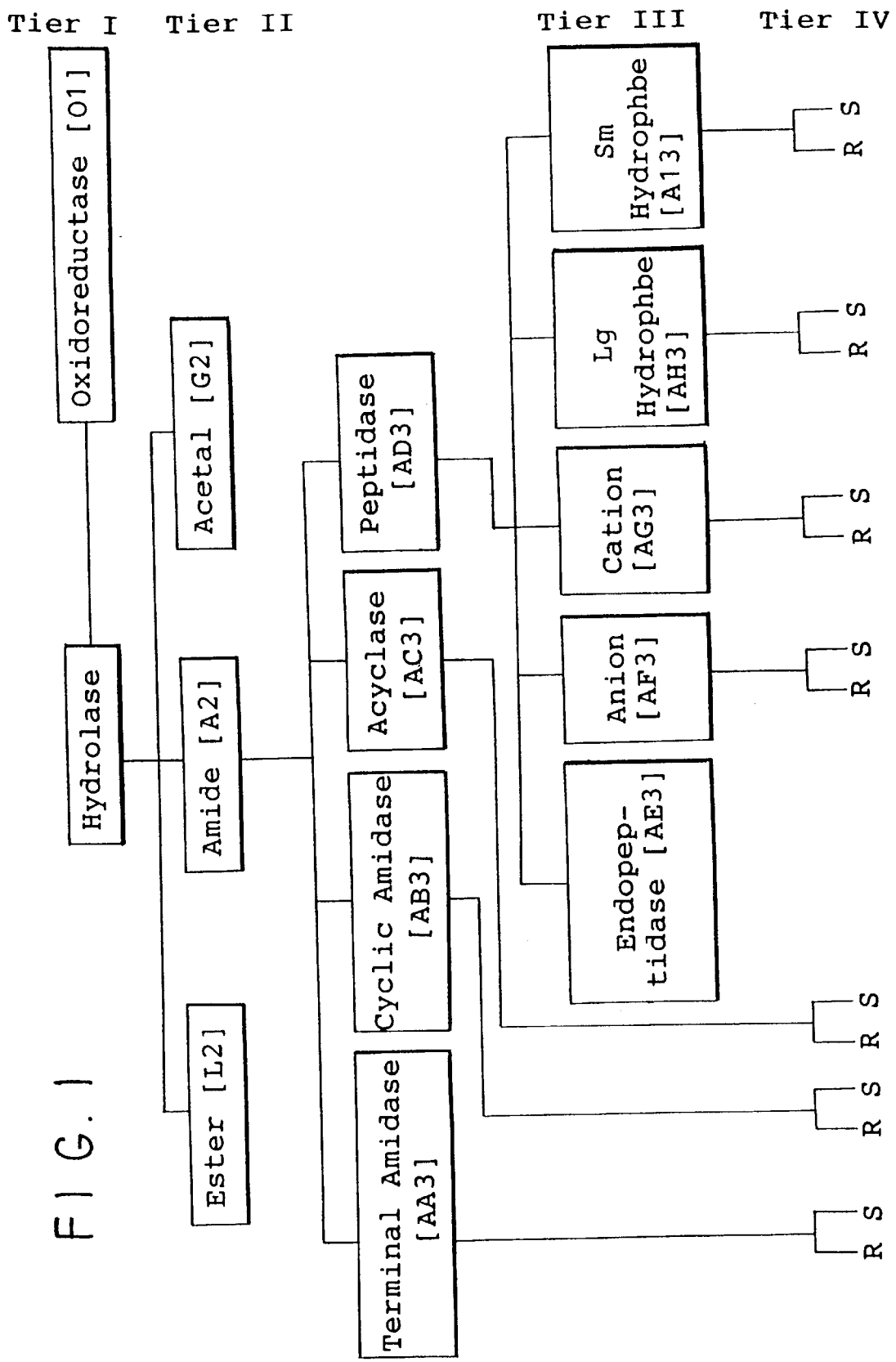
FIG. 1 is a schematic representation of one embodiment of various tiers of chemical characteristics of an enzyme which may be employed in the present invention.

The invention will be further described with reference to the following examples; however, the scope of the present invention is not to be limited thereby. Unless otherwise specified, all parts are by weight.

EXAMPLE 1

Production of Expression Library

The following describes a representative procedure for preparing an expression library for screening by the tiered approach of the present invention.

One gram of Thermococcus GU5L5 cell pellet was lysed and the DNA isolated by literature procedures[1]. Approximately 100 µg of the isolated DNA was resuspended in TE buffer and vigorously passed through a 25 gauge double-hubbed needle until the sheared fragments were in the size range of 0.5–10.0 Kb (3.0 Kb average). The DNA ends were "polished" or blunted with Mung Bean Nuclease (300 units, 37° C., 15 minutes), and EcoRI restriction sites in the target DNA protected with EcoRI Methylase (200 units, 37° C., 1 hour). EcoRI linkers [GGAATTCC] were ligated to the blunted/protected DNA using lopmole ends of linkers to 1pmole end of target DNA. The linkers were cut back with EcoRI restriction endonuclease (200 units, 37° C., 1.5 hours) and the DNA size fractionated by sucrose gradient (Maniatis, T., Fritsch, E. F., and Sambrook, J. *Molecular Cloning*, Cold Spring Harbor Press, New York, 1982). The prepared target DNA was ligated to the Lambda ZAP® II vector (Stratagene), packaged using in vitro lambda packaging extracts and grown on XL1-Blue MRF' *E.coli* strain according to the manufacturer. The pBluescript® phagemids were excised from the lambda library, and grown in *E.coli* DH10B F' kan, according to the method of Hay and Short[2]. The resulting colonies were picked with sterile toothpicks and used to singly inoculate each of the wells of 11 96-well microtiter plates (1056 clones in all). The wells contained 250 µL of LB media with 100 µg/mL ampicillin, 80 µg/mL methicillin, and 10% v/v glycerol (LB Amp/Meth, glycerol). The cells were grown overnight at 37° C. without shaking. This constituted generation of the "Source Library"; each well of the Source Library thus contained a stock culture of *E.coli* cells, each of which contained a pBluescript phagemid with a unique DNA insert.

[1] current Protocols in Molecular Biology (1987) 2.4.1.
[2] Hay, B. and Short, J. Strategies. 1992, 5, 16.

EXAMPLE 2

The following is a representative example of a procedure for screening an expression library prepared in accordance with Example 1. In the following, the chemical characteristic Tiers are as follows:
Tier 1: Hydrolase
Tier 2: Amide, Ester and Acetal
Tier 3: Divisions and subdivisions are based upon the differences between individual substrates which are covalently attached to the functionality of Tier 2 undergoing reaction; as well as substrate specificity.
Tier 4: The two possible enantiomeric products which the enzyme may produce from a substrate.

Although the following example is specifically directed to the above mentioned tiers, the general procedures for testing for various chemical characteristics is generally applicable to substrates other than those specifically referred to in this Example.

Screening for Tier 1-hydrolase; Tier 2-amide.

The eleven plates of the Source Library were used to multiply inoculate a single plate (the "Condensed Plate") containing in each well 200 µL of LB Amp/Meth, glycerol. This step was performed using the High Density Replicating Tool (HDRT) of the Beckman Biomek with a 1% bleach, water, isopropanol, air-dry sterilization cycle in between each inoculation. Each well of the Condensed Plate thus contained 11 different pBluescript clones from each of the eleven source library plates. The Condensed Plate was grown for 2h at 37° C. and then used to inoculate two white 96-well Dynatech microtiter daughter plates containing in each well 250 µL of LB Amp/Meth, glycerol. The original condensed plates was incubated at 37° C. for 18h then stored at −80° C. The two condensed daughter plates were incubated at 37° C. also for 18h. The condensed daughter plates were then heated at 70° C. for 45 min. to kill the cells and inactivate the host *E.coli* enzymes. A stock solution of 5 mg/mL morphourea phenylalanyl-7-amino-4-trifluoromethyl coumarin (MuPheAFC, the 'substrate') in DMSO was diluted to 600 µM with 50 mM pH 7.5 Hepes buffer containing 0.6 mg/mL of the detergent dodecyl maltoside.

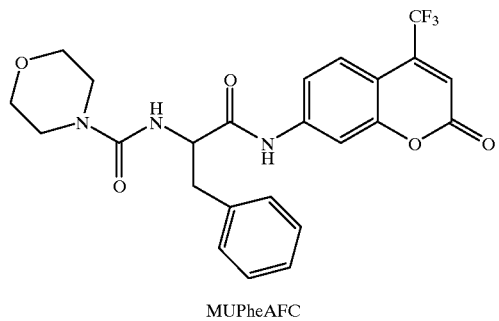

MUPheAFC

Fifty µL of the 600 µM MuPheAFC solution was added to each of the wells of the white condensed plates with one 100 µL mix cycle using the Biomek to yield a final concentration of substrate of ~100 µM. The fluorescence values were recorded (excitation=400 nm, emission=505 nm) on a plate reading fluorometer immediately after addition of the substrate (t=0). The plate was incubated at 70° C. for 100 min, then allowed to cool to ambient temperature for 15 additional minutes. The fluorescence values were recorded again (t=100). The values at t=0 were subtracted from the values at t=100 to determine if an active clone was present.

This data indicated that one of the eleven clones in well G8 was hydrolyzing the substrate. In order to determine the individual clone which carried the activity, the eleven source library plates were thawed and the individual clones used to singly inoculate a new plate containing LB Amp/Meth, glycerol. As above, the plate was incubated at 37° C. to grow the cells, heated at 70° C. to inactivate the host enzymes, and 50 µL of 600 µM MuPheAFC added using the Biomek. Additionally three other substrates were tested. The methyl umbelliferone heptanoate, the CBZ-arginine rhodamine derivative, and fluorescein-conjugated casein (~3.2 mol fluorescein per mol of casein).

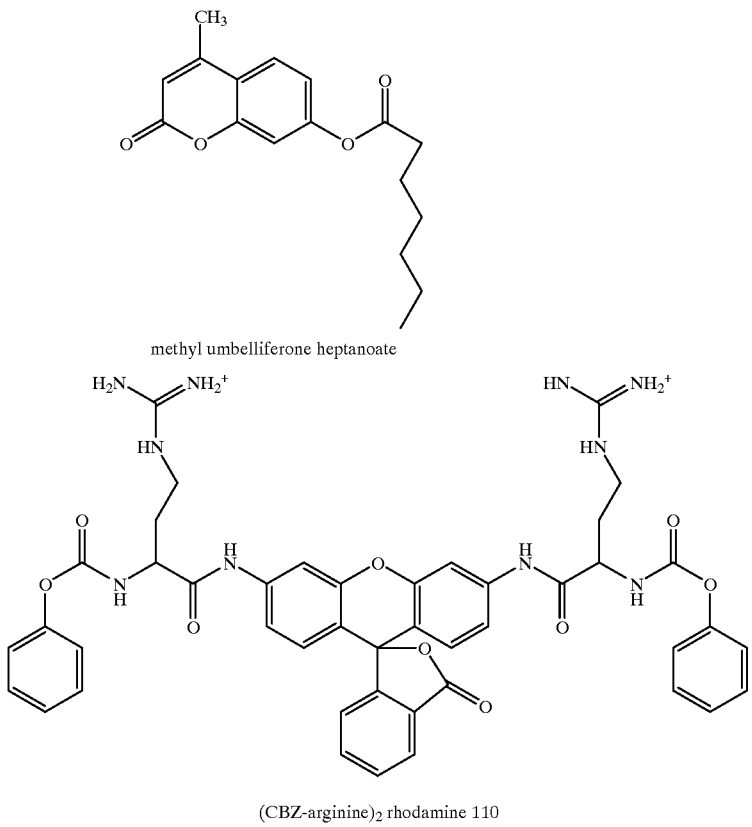

methyl umbelliferone heptanoate (CBZ-arginine)₂ rhodamine 110

The umbelliferone and rhodamine were added as 600 μM stock solutions in 50 μL of Hepes buffer. The fluorescein conjugated casein was also added in 50 μL at a stock concentration of 20 and 200 mg/mL. After addition of the substrates the t=0 fluorescence values were recorded, the plate incubated at 70° C., and the t=100 min. values recorded as above.

This data indicated that the active clone was in plate 2. The arginine rhodamine derivative was also turned over by this activity, but the lipase substrate, methyl umbelliferone heptanoate, and protein, fluorescein-conjugated casein, did not function as substrates.

Based on the above data the Tier 1 classification is 'hydrolase' and the Tier 2 classification is amide bond. There is no cross reactivity with the Tier 2-ester classification.

As shown in FIG. 1, a recombinant clone from the library which has been characterized in Tier 1 as hydrolase and in Tier 2 as amide may then be tested in Tier 3 for various specificities. In FIG. 1, the various classes of Tier 3 are followed by a parenthetical code which identifies the substrates of Table 1 which are used in identifying such specificities of Tier 3.

Figure 2:
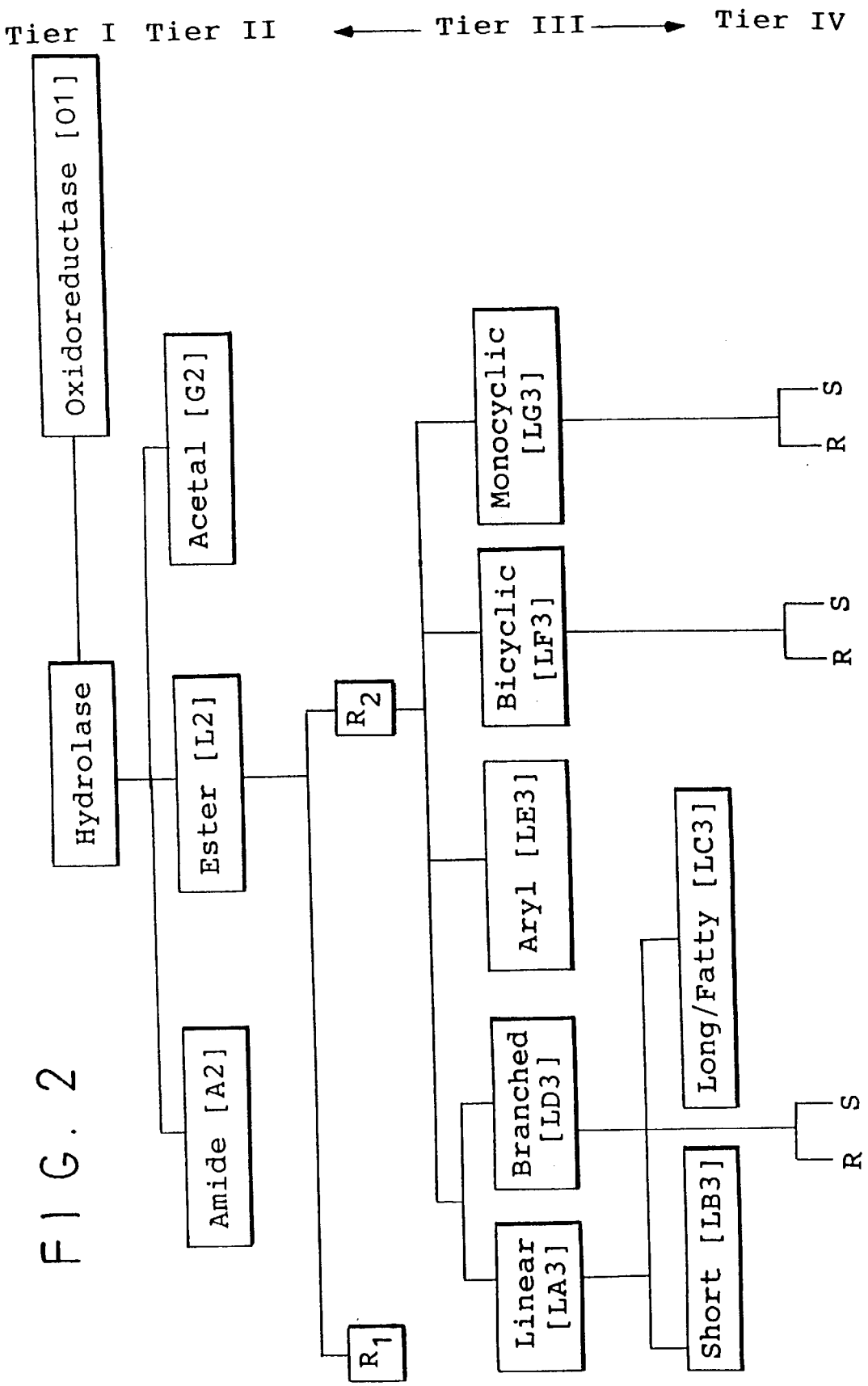
FIG. 2 is a schematic representation of another embodiment of various tiers of chemical characteristics of an enzyme which may be employed in the present invention.
Figure 3:
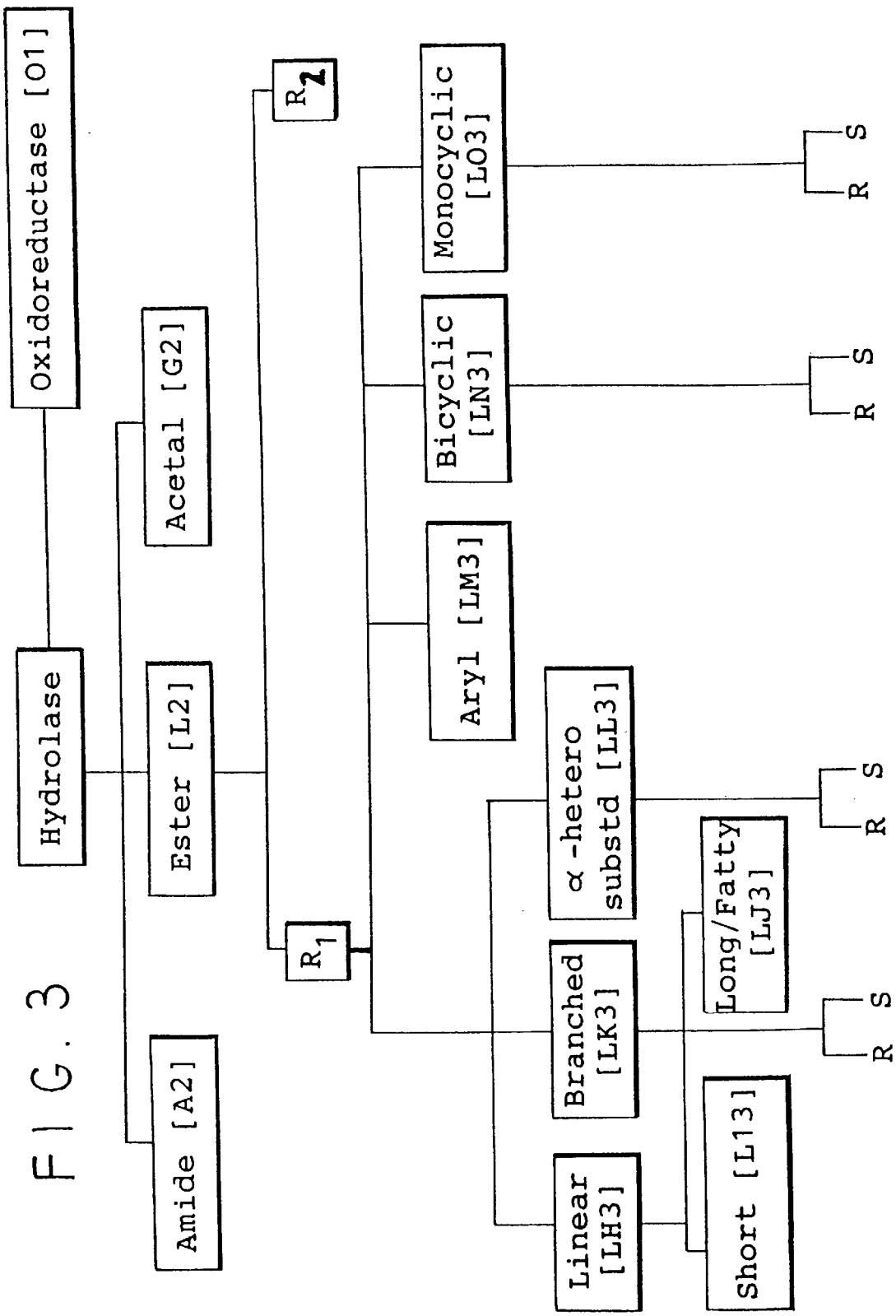
FIG. 3 is a schematic representation of a further embodiment of various tiers of chemical characteristics of an enzyme which may be employed in the present invention.

As shown in FIGS. 2 and 3, a recombinant clone from the library which has been characterized in Tier 1 as hydrolase and in Tier 2 as ester may then be tested in Tier 3 for various specificities. In FIGS. 2 and 3, the various classes of Tier 3 are followed by a parenthetical code which identifies the substrates of Tables 2 and 2 which are used in identifying such specificities of Tier 3. In FIGS. 2 and 3, $R_2$ represents the alcohol portion of the ester and $R_1$ represents the acid portion of the ester.

Figure 4:
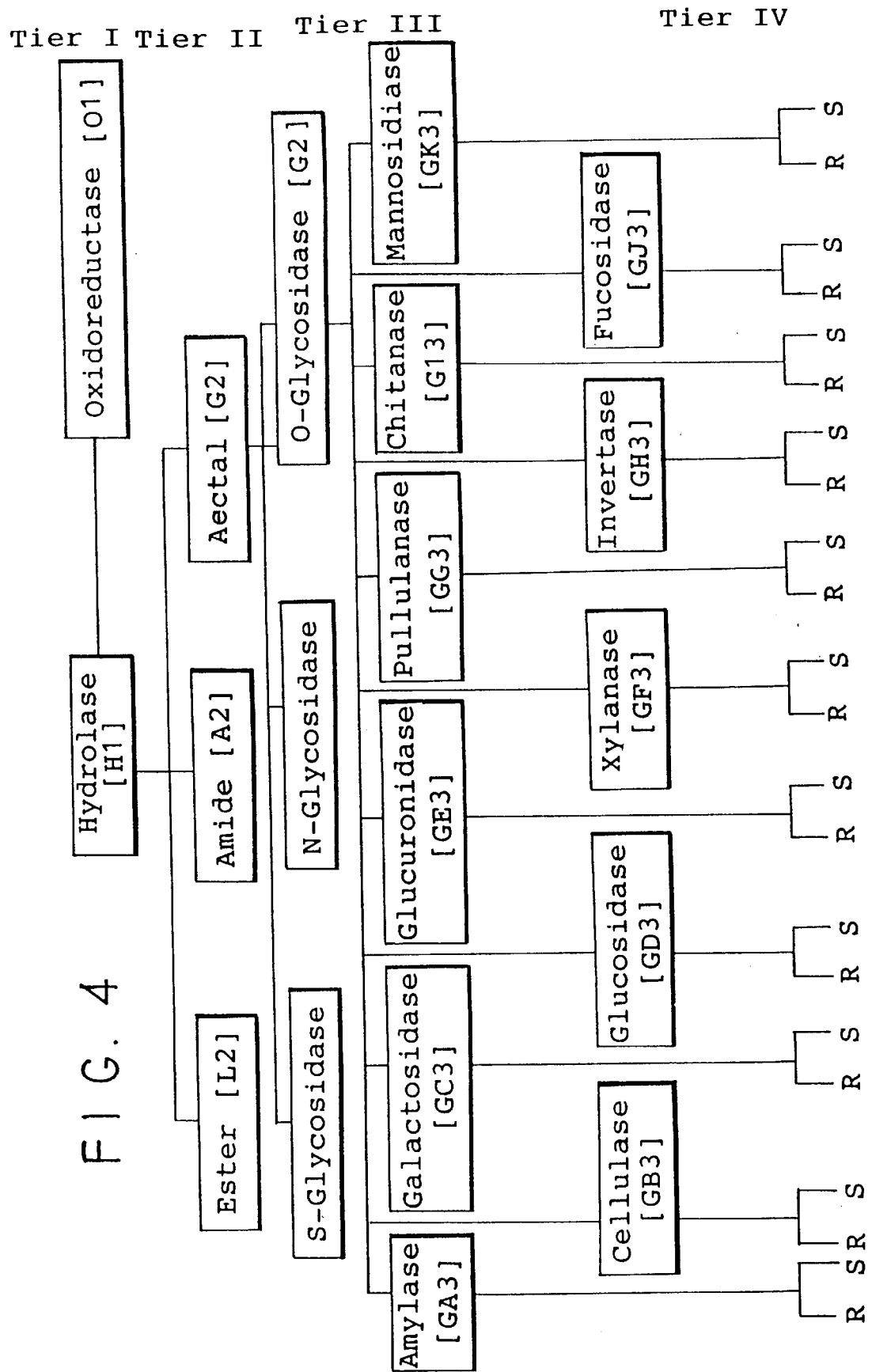
FIG. 4 is a schematic representation of a still further embodiment of various tiers of chemical characteristics of an enzyme which may be employed in the present invention.

As shown in FIG. 4, a recombinant clone from the library which has been characterized in Tier 1 as hydrolase and in Tier 2 as acetal may then be tested in Tier 3 for various specificities. In FIG. 4, the various classes of Tier 3 are followed by a parenthetical code which identifies the substrates of Table 4 which are used in identifying such specificities of Tier 3.

Enzymes may be classified in Tier 4 for the chirality of the product(s) produced by the enzyme. For example, chiral amino esters may be determined using at least the following substrates:

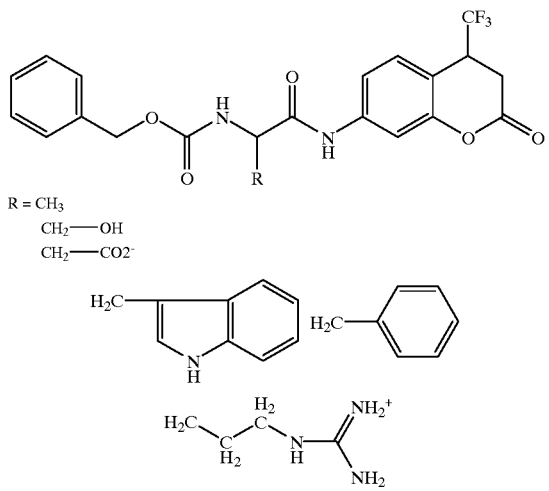

R = CH₃
 CH₂—OH
 CH₂—CO2⁻

For each substrate which is turned over the enantioselectivity value, E, is determined according to the equation below[3]:

$$E = \frac{\ln[(1-c(1+ee_p)]}{\ln[(1-c(1-ee_p)]}$$

where $ee_p$=the enantiomeric excess (ee) of the hydrolyzed product and c=the percent conversion of the reaction.

[3]Wong and Whitesides, Enzymes in Synthetic Organic Chemistry, 1994, Elsevier, Tarrytown, N.Y., pp. 9–12.

The enantiomeric excess is determined by either chiral high performance liquid chromatography (HPLC) or chiral capillary electrophoresis (CE). Assays are performed as follows: two hundred μL of the appropriate buffer is added to each well of a 96-well white microtiter plate, followed by 50 μL of partially or completely purified enzyme solution; 50 μL of substrate is added and the increase in fluorescences monitored versus time until 50% of the substrate is consumed or the reaction stops, which ever comes first.

EXAMPLE 3

This Example 3 describes procedures for testing for certain physical characteristics of recombinant clones of a library.

pH Optima.

Two hundred μL of the appropriate pH and ionic strength, temperature equilibrated buffer[4] is added to each well of a 96-well white microtiter plate, followed by 50 μL of partially or completely purified enzyme solution; 50 μL of substrate at 5× $K_M$ (final concentration) or the solubility limit, which ever is lower, is added to initiate the reaction and the increase in fluorescence monitored versus time. The rate of reaction at a defined temperature is determined under initial velocity (linear) conditions.

[4]Ellis, K. J. and Morrison, J. F. Methods in Enzymology, 1982, 87, 405.

Temperature Optima.

Two hundred μL of the optimal pH and ionic strength, temperature equilibrated buffer is added to each well of a 96-well white microtiter plate, followed by 50 μL of partially or completely purified enzyme solution; 50 μL of substrate at 5× $K_M$ or the solubility limit, which ever is lower, is added to initiate the reaction and the increase in fluorescence monitored versus time. The temperature of the incubation is varied. The rate of reaction is determined under initial velocity (linear) conditions.

Temperature Stability.

Reactions are performed as described for Temperature optima except that substrate is added at selected time points during the incubation and the initial velocity determined. The decrease in activity (if present) is fit to a single exponential function to determine the rate and half life of inactivation.

Metal Ion Selectivity.

Two hundred μL of the optimal pH and ionic strength, temperature equilibrated buffer is added to each well of a 96-well white microtiter plate, followed by 50 μL of partially or completely purified enzyme solution; 50 μL of substrate at 5× $K_M$ or the solubility limit, which ever is lower, and the desired metal ion or EDTA at 6× the indicated concentration is added to initiate the reaction, and the increase in fluorescence monitored versus time. The rate of reaction is determined under initial velocity (linear) conditions.

Detergent Sensitivity.

Two hundred μL of the optimal pH and ionic strength, temperature equilibrated buffer is added to each well of a 96-well white microtiter plate, followed by 50 μL of partially or completely purified enzyme solution; 50 μL of substrate at 5× $K_M$ or the solubility limit, which ever is lower, and the desired detergent at 6× the indicated concentration is added to initiate the reaction, and the increase in fluorescence monitored versus time. The rate of reaction is determined under initial velocity (linear) conditions.

Organic Solvent Tolerance.

Water Miscible.

Two hundred μL of buffer and dimethylformamide (DMF). mixture (see table below) is added to each well of a 96-well white microtiter plate, followed by 30 μL of partially or completely enzyme solution; 50 μL of substrate at 5× $K_M$ or the solubility limit, which ever is lower in 100% DMF is added to initiate the reaction, and the increase in flourescence monitored versus time. The rate of reaction is determine under initial velocity (linear) conditions.

| μL DMF | μL Buffer | % DMF final |
|--------|-----------|-------------|
| 200    | 0         | 90          |
| 175    | 25        | 75          |
| 130    | 70        | 60          |
| 85     | 115       | 45          |
| 40     | 160       | 30          |

Water Immiscible.

Two hundred μL of hexane or toluene is added to each well of a 96-well white microtiter plate, followed by 50 μL of partially or completely purified enzyme solution; 50 μL of substrate at 5× $K_M$ or the solubility limit, which ever is lower in buffer is added to initiate the reaction, and the increase in fluorescence monitored versus time. The reaction is shaken at 100 RPM. The rate of reaction is determined under initial velocity (linear) conditions.

Numerous modifications and variations of the present invention are possible in light of the above teachings; therefore, within the scope of the claims, the invention may be practiced other than as particularly described.

TABLE 1

A2
Fluorescein conjugated casein
(3.2 mol fluorescein /mol casein)

CBZ—Ala—AMC
t-BOC—Ala—Ala—Asp—AMC
succinyl-Ala—Gly—Leu—AMC
CBZ—Arg—AMC
CBZ—Met—AMC
morphourea-Phe—AMC

AA3

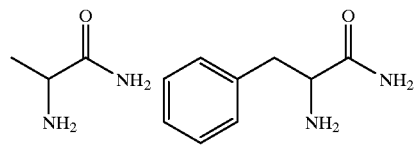

AB3

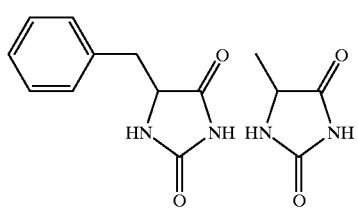

TABLE 1-continued

AC3

[structure: two amino acid derivatives — N-acetyl alanine and N-acetyl phenylalanine carboxylates]

AD3

Fluorescein conjugated casein t-BOC—Ala—Ala—Asp—AFC
CBZ—Ala—Ala—Lys—AFC
succinyl-Ala—Ala—Phe—AFC
succinyl-Ala—Gly—Leu—AFC

AE3

Fluorescein conjugated casein

AF3 t-BOC—Ala—Ala—Asp—AFC
CBZ—Asp—AFC

AG3

CBZ—Ala—Ala—Lys—AFC
CBZ—Arg—AFC

AH3 succinyl-Ala—Ala—Phe—AFC
CBZ—Phe—AFC
CBZ—Trp—AFC

AI3 succinyl-Ala—Gly—Leu—AFC
CBZ—Ala—AFC
CBZ—Sewr—AFC t-BOC = t-butoxy carbonyl, CBZ = carbonyl benzyloxy.
AMC = 7-amino-4-methyl coumarin
AFC = 7-amino-4-trifluoromethyl coumarin.)

TABLE 2

L2

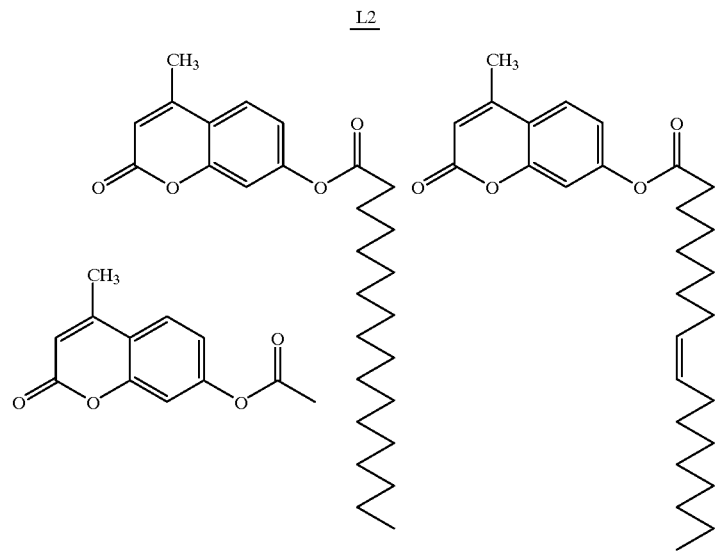

TABLE 2-continued
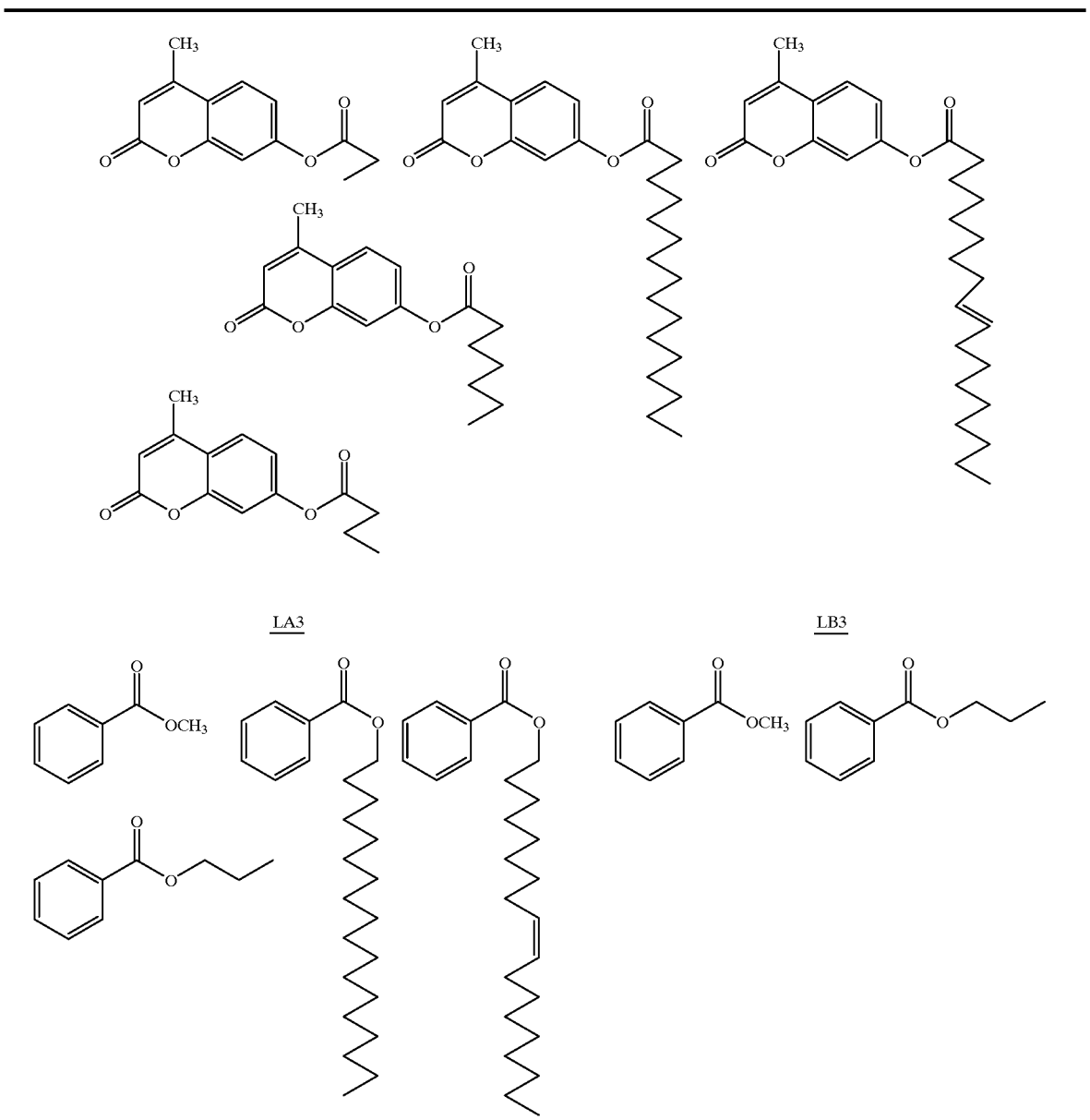

TABLE 2-continued
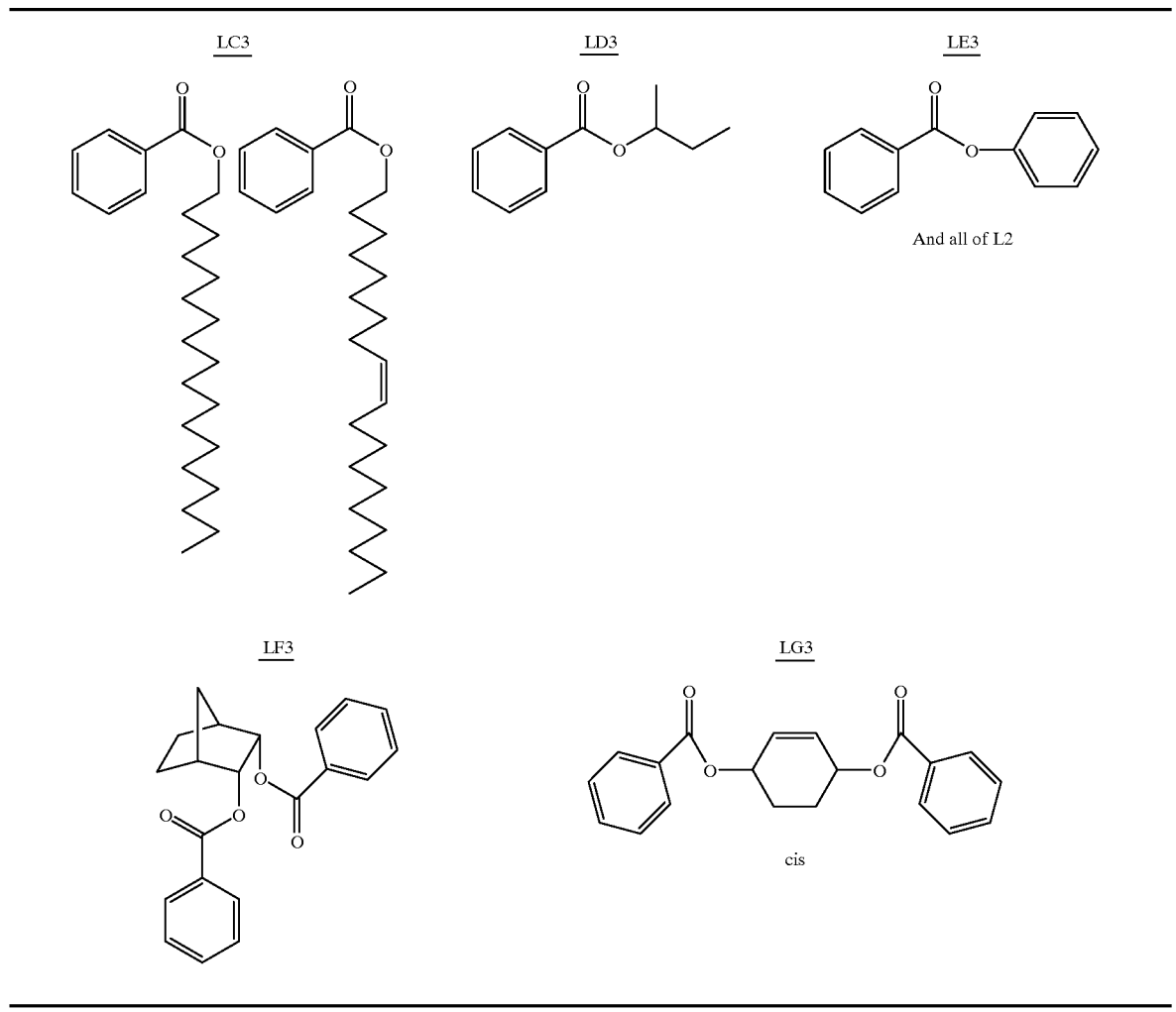
TABLE 3
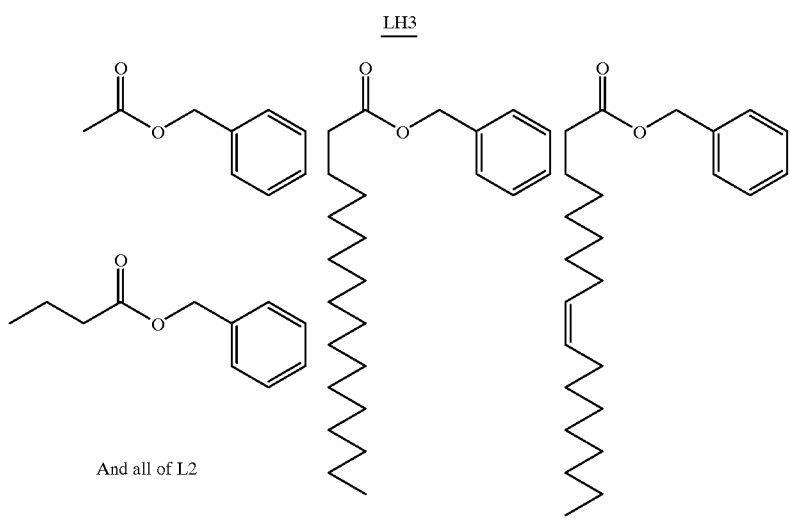

TABLE 3-continued
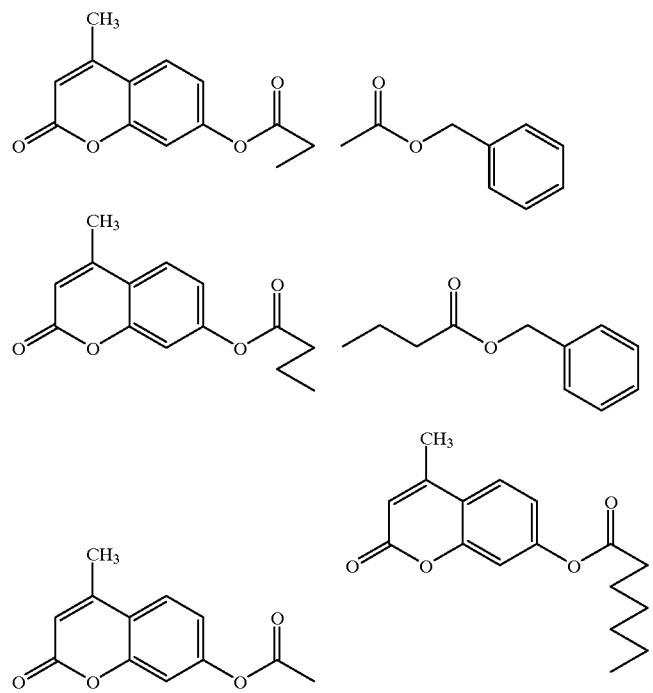
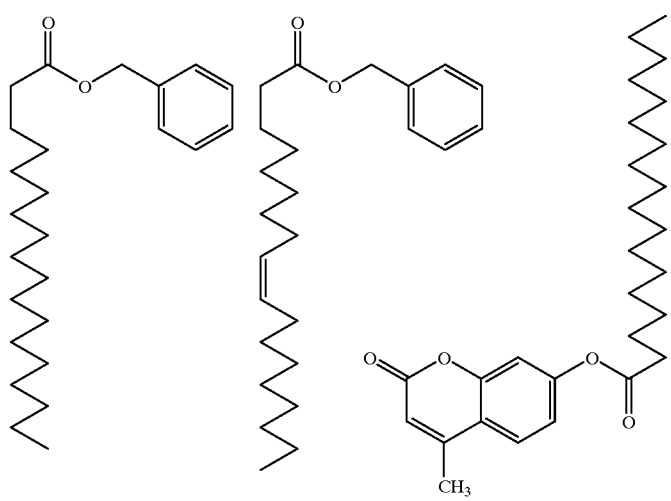

TABLE 3-continued
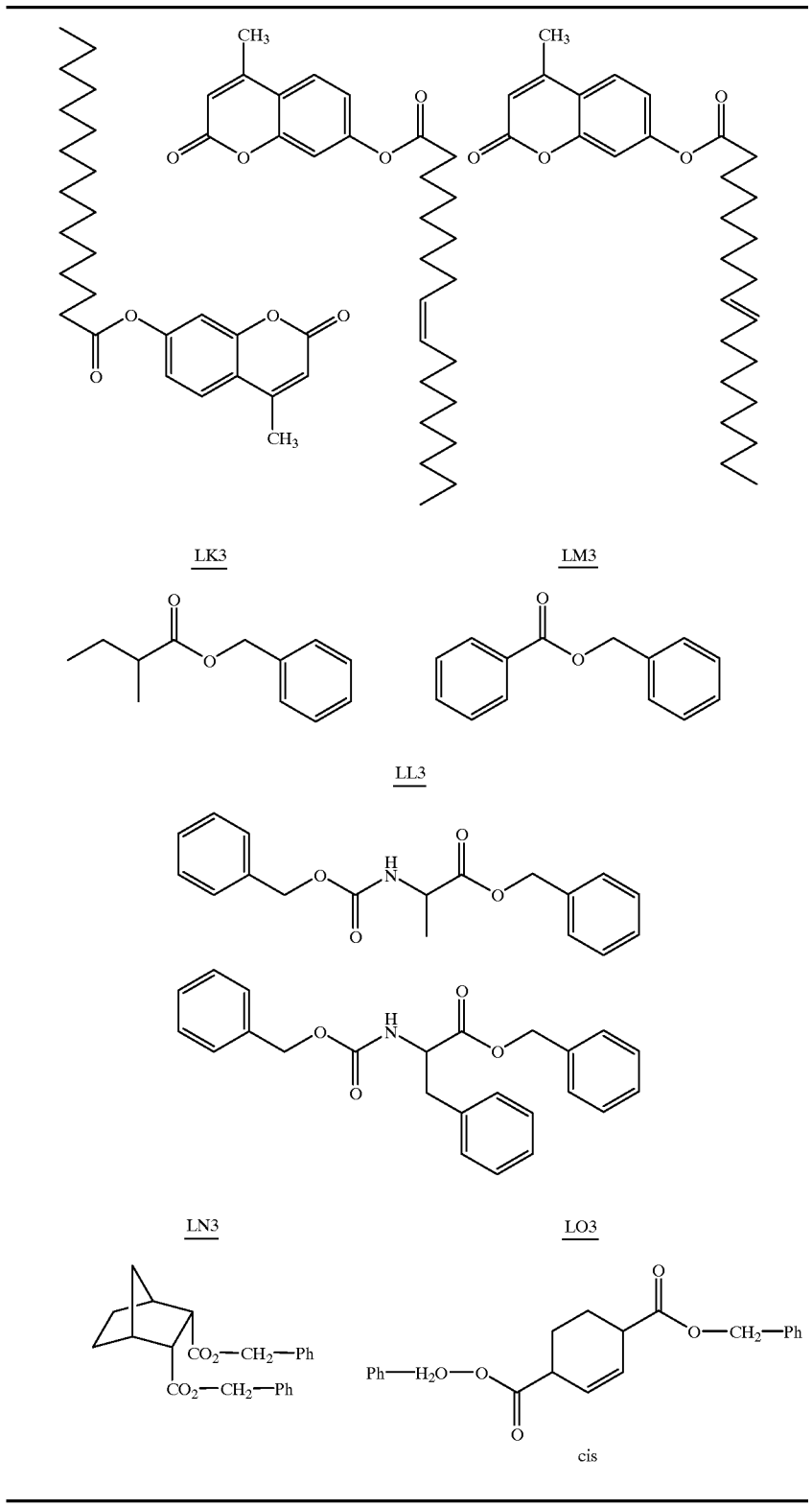

TABLE 4

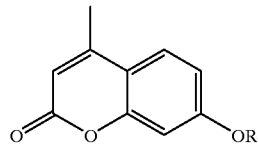

4-methyl umbelliferone wherein R =

| | |
|---|---|
| G2 | β-D-galactose |
| | β-D-glucose |
| | β-D-glucuronide |
| GB3 | β-D-cellotrioside |
| | β-D-cellobiopyranoside |
| GC3 | β-D-galactose |
| | α-D-galactose |
| GD3 | β-D-glucose |
| | α-D-glucose |
| GE3 | β-D-glucuronide |
| GI3 | β-D-N,N-diacetylchitobiose |
| GJ3 | β-D-fucose |
| | α-L-fucose |
| | β-L-fucose |
| GK3 | β-D-mannose |
| | α-D-mannose |
| | non-Umbelliferyl substrates |
| GA3 | amylose [polyglucan α1,4 linkages], amylopectin [polyglucan branching α1,6 linkages] |

TABLE 4-continued

| | |
|---|---|
| GF3 | xylan [poly 1,4-D-xylan] |
| GG3 | amylopectin, pullulan |
| GH3 | sucrose, fructofuranoside |

What is claimed is:

1. A kit comprising at least one container containing a mixture of enzymes, wherein said enzymes are obtained by culturing a gene expression library, comprising a pool of expression constructs, each expression construct comprising a vector containing one or more cDNA or genomic DNA fragments, wherein the cDNA or genomic DNA fragments in the pool of expression constructs are derived from a plurality of species of uncultured donor microorganisms, and wherein the cDNA or genomic DNA fagments are each operably-associated with one or more regulatory regions that drives expression of genes encoded by the cDNA or genomic DNA fragments in an appropriate host organism, wherein the enzyme is selected from the group consisting of oxidoreductase, transferase, hydrolase, lyase, isomerase, and ligase activity.

2. The method of claim 1, wherein the microorganisms are derived from an environmental sample.

* * * * *

UNITED STATES PATENT AND TRADEMARK OFFICE
CERTIFICATE OF CORRECTION

PATENT NO.    : 6,004,788
DATED         : December 21, 1999
INVENTOR(S)   : Short Page 1 of 1

It is certified that error appears in the above-identified patent and that said Letters Patent is hereby corrected as shown below:

Column 26, claim 1,
Line 17, replace "genomic DNA fagments" with -- genomic DNA fragments. --

Signed and Sealed this

Twenty-sixth Day of March, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,004,788
DATED : December 21, 1999
INVENTOR(S) : Jay Short

It is certified that error appears in the above-identified patent and that said Letters Patent is hereby corrected as shown below:

<u>Column 26,</u>
Line 25, please replace the "The method of claim 1..." with -- A kit of claim 1... --

Signed and Sealed this

Ninth Day of November, 2004

JON W. DUDAS
*Director of the United States Patent and Trademark Office*